US012668802B2

(12) United States Patent      (10) Patent No.:   US 12,668,802 B2
Chen et al.                  (45) Date of Patent:     Jun. 30, 2026

(54) APPLICATION OF HELZ2 IN DRUGS FOR PREVENTING AND TREATING TUMORS

(71) Applicant: JIANGSU CONCORD BIOTECHNOLOGY CO., LTD, Zhenjiang (CN)

(72) Inventors: Huabiao Chen, Zhenjiang (CN); Tao Li, Zhenjiang (CN)

(73) Assignee: JIANGSU CONCORD BIOTECHNOLOGY CO., LTD, Zhenjiang (CN)

( * ) Notice: Subject to any disclaimer, the term of this patent is extended or adjusted under 35 U.S.C. 154(b) by 911 days.

(21) Appl. No.: 17/979,153

(22) Filed: Nov. 2, 2022

(65) Prior Publication Data

US 2023/0416749 A1     Dec. 28, 2023

Related U.S. Application Data

(63) Continuation of application No. PCT/CN2022/105592, filed on Jul. 14, 2022.

(30) Foreign Application Priority Data

Jun. 23, 2022    (CN) ......................... 202210725149.0

(51) Int. Cl.
| | |
|---|---|
| *C12N 15/113* | (2010.01) |
| *A61K 49/00* | (2006.01) |
| *A61P 35/00* | (2006.01) |
| *C12N 9/22* | (2006.01) |
| *C12N 15/11* | (2006.01) |
| *C12N 15/86* | (2006.01) |
| *C12N 15/90* | (2006.01) |

(52) U.S. Cl.
CPC ...... *C12N 15/1137* (2013.01); *A61K 49/0008* (2013.01); *A61P 35/00* (2018.01); *C12N 9/22* (2013.01); *C12N 15/11* (2013.01); *C12N 15/86* (2013.01); *C12N 15/907* (2013.01); *C12N 2310/20* (2017.05); *C12N 2310/531* (2013.01); *C12N 2740/15043* (2013.01); *C12N 2800/80* (2013.01)

(58) Field of Classification Search
None
See application file for complete search history.

(56) References Cited

FOREIGN PATENT DOCUMENTS

WO       2021097437 A1    5/2021

OTHER PUBLICATIONS

Doyle, A., McGarry, M.P., Lee, N.A. et al. The construction of transgenic and gene knockout/knockin mouse models of human disease. Transgenic Res 21, 327-349 (2012). https://doi.org/10.1007/s11248-011-9537-3 (Year: 2012).*
Satoshi Yoshino et al. Protection Against High-Fat Diet-Induced Obesity in Helz2-Deficient Male Mice Due to Enhanced Expression of Hepatic Leptin Receptor, Endocrinology, vol. 155, Issue 9, Sep. 1, 2014, pp. 3459-3472, https://doi.org/10.1210/en.2013-2160 (Year: 2014).*
Satoshi Yoshino et al. "Protection against high-fat diet-induced obesity in Helz2-deficient male mice due to enhanced expression of hepatic leptin receptor." Endocrinology 155.9 (2014): 3459-3472.
Hanjun Dai et al. "HELZ2 promotes K63-linked polyubiquitination of c-Myc to induce retinoblastoma tumorigenesis." Medical Oncology 39 (2022): 1-8.
Hanjun Dai et al.,HELZ2 promotes K63-linked polyubiquitination of c-Myc to induce retinoblastoma tumorigenesis, Springer Science+ Business Media, LLC, part of Springer Nature 2021, Nov. 10, 2021.

* cited by examiner

*Primary Examiner* — Anne M. Gussow
*Assistant Examiner* — Nura M. Choudhury
(74) *Attorney, Agent, or Firm* — Anova Law Group, PLLC

(57) ABSTRACT

The present disclosure provides a vector containing a target sequence that targets and interferes with Helicase with zinc finger 2 (Helz2), the target sequence comprising one or more of the following sequences:

SEQ ID No. 5:
5'-GCTATCAAGTCTGTCACTACT-3';

SEQ ID No. 6:
5'-GCACGATGCTGTATGGCTTTG-3';

SEQ ID No. 7:
5'-GGGCCTCATTGACACTCAAAG-3'.

4 Claims, 7 Drawing Sheets

Specification includes a Sequence Listing.

APPLICATION OF HELZ2 IN DRUGS FOR PREVENTING AND TREATING TUMORS

CROSS-REFERENCES TO RELATED APPLICATIONS

This application is a continuation application of PCT Patent Application No. PCT/CN2022/105592, filed on Jul. 14, 2022, which claims priority to Chinese Patent Application No. 202210725149.0, filed on Jun. 23, 2022, the entire contents of all of which are incorporated herein by reference.

REFERENCE TO AN ELECTRONIC SEQUENCE LISTING

The contents of the electronic sequence listing (seqlisting001630018.xml; Size: 7,221 bytes; and Date of Creation: Oct. 27, 2022) is herein incorporated by reference in its entirety.

FIELD OF THE DISCLOSURE

The present disclosure relates to preparation of gene therapy drugs, and in particular to an application of Helz2 in drugs for preventing and treating tumors.

BACKGROUND

Helicase with zinc finger 2 (Helz2) [OMIM 611265], also known as PRIC285 or PDIP1, is a karyolytic zymoprotein containing 2,649 amino acids, as well as a part of a peroxisome proliferator activated receptor a interacting complex (PRIC). Helz2 consists of two ATP-binding sequences, one RNaseB structural domain and a dual DNA/RNA helicase sequence. Helz2 is involved in multiple mechanisms related to gene regulation, including gene transcription, mRNA modification and DNA repair. Helz2 can act as a nuclear transcriptional co-activator of PPARα, PPARγ and other nuclear receptors (RXRA, THRA and THRB). In addition, Helz2 was found to have antiviral function in mammals, and this gene was identified as an interferon stimulated gene (ISG) containing conserved components of antiviral immunity. Moreover, Helz2 was also found to have a mediating role in an antiviral response of interferon, the mediating role involving Helz2 transcription, up-regulation of nuclear proteins, and activation of a transcriptional program.

However, there is no report on research or application of Helz2 knockout mouse models in anti-tumor aspect. To further illustrate influence of decreased expression level of Helz2 on occurrence and development of tumors, there is a need to construct Helz2 knockout mouse model and conduct tumor modeling for the mice, and provide animal models for exploring mechanism of Helz2 in affecting tumor cell growth, its role in inhibiting occurrence and development of tumors, and exploring new methods for treating and/or preventing tumors. In addition, there is neither research or application corresponding to homozygous Helz2 knockout mouse model using a CRISPR/Cas9 system, nor research or application of a sequence targeting Helz2 or its expressed product in tumor therapy.

The disclosed methods and applications are directed to solve one or more problems set forth above and other problems.

SUMMARY

One aspect of the present disclosure provides a vector containing a target sequence that targets and interferes with Helicase with zinc finger 2 (Helz2), the target sequence comprising one or more of the following sequences:

```
SEQ ID No. 5:
5'-GCTATCAAGTCTGTCACTACT-3';

SEQ ID No. 6:
5'-GCACGATGCTGTATGGCTTTG-3';

SEQ ID No. 7:
5'-GGGCCTCATTGACACTCAAAG-3'.
```

Another aspect of the present disclosure provides a method for establishing an Helz2 knockout mouse model, including: performing Helz2 knockout on fertilized mouse eggs by using CRISPR/Cas9 technique with an sgRNA sequence; and obtaining a systemic Helz2 knockout homozygous mouse model through microinjection and breeding of the fertilized mouse eggs.

Another aspect of the present disclosure provides an sgRNA sequence for establishing an Helz2 knockout animal model, the sgRNA sequence including one or more of the following sequences:

```
SEQ ID No. 1:
5'-GCCCCAGAGTTACCAGATGGAGG-3';

SEQ ID No. 2:
5'-CCTACACCCGACAGAGGTGTAGG-3';

SEQ ID No. 3:
5'-AGCAGTGACAGTCTTATGGGTGG-3';

SEQ ID No. 4:
5'-GGCATACAGAGGATTGCCACAGG-3'.
```

Another aspect of the present disclosure provides a drug for treating or preventing a tumor. The drug includes a product targeting an Helz2 gene or targeting an expression of the Helz2 gene.

Other aspects of the present disclosure can be understood by those skilled in the art in light of the description, the claims, and the drawings of the present disclosure.

BRIEF DESCRIPTION OF THE DRAWINGS

The embodiments are shown and clarified with reference to the drawings. These drawings serve to clarify the basic principle, so that only aspects necessary for understanding the basic principle are shown. The drawings are not to scale. In the drawings, the same reference numerals indicate similar features.

Other features, characteristics, advantages and benefits of the present disclosure will become more apparent through the following detailed description in conjunction with the accompanying drawings.

DETAILED DESCRIPTION

In the following detailed description of the preferred embodiments, reference will be made to the accompanying drawings constituting a part of the present disclosure. The drawings show specific embodiments capable of implementing the present disclosure by way of example. The exemplary embodiments are not intended to be exhaustive of all embodiments according to the present disclosure. It can be understood that other embodiments can be utilized, and structural or logical modifications can also be made without departing from the scope of the present disclosure. Therefore, the following detailed description is not restrictive, and the scope of the present disclosure is defined by the appended claims.

The present disclosure provides a method for establishing an Helz2 knockout mouse model. The Helz2 knockout can be performed on fertilized mouse eggs using CRISPR/Cas9 technology, and through microinjection and breeding of the fertilized mouse eggs, a systemic Helz2 knockout homozygous mouse model (Helz2-Cas9-KO) can be obtained. The method provides a desired animal model for exploring the mechanism between Helz2 and tumors, and also provides support for application of the Helz2-Cas9-KO mouse model in preparation or screening of drugs for treating and/or preventing tumors.

Figure 1:
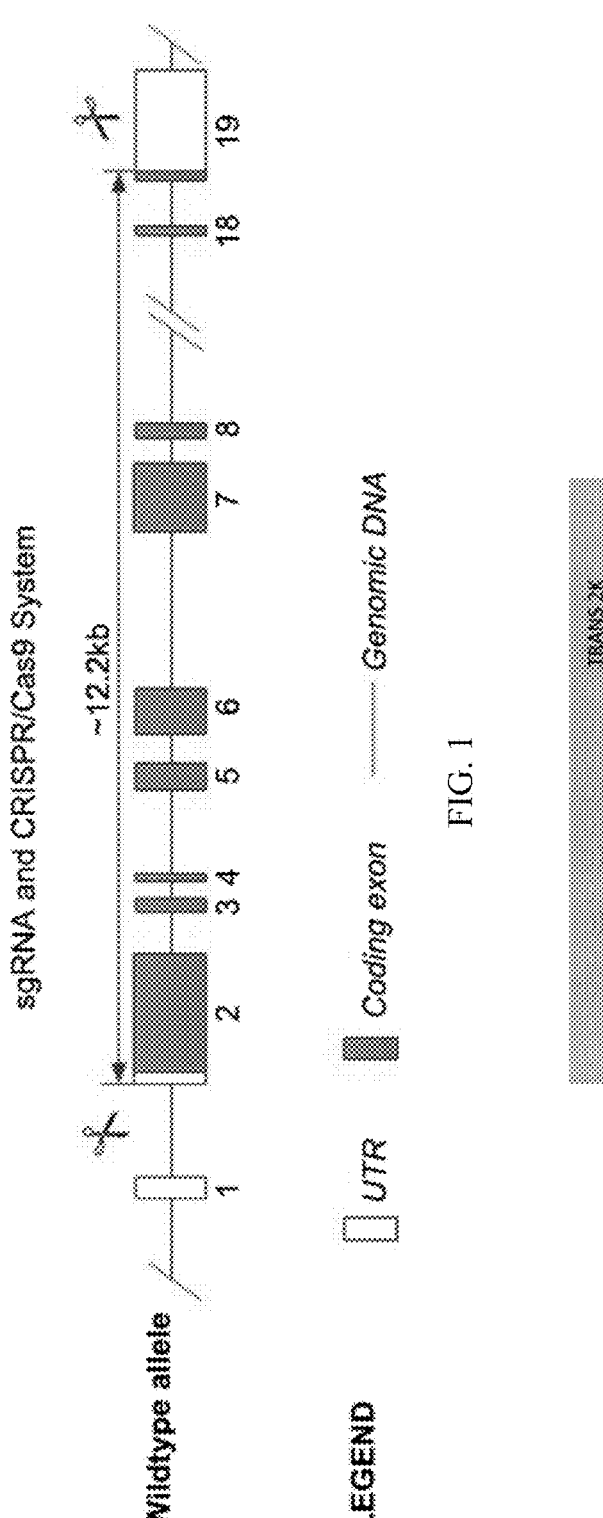
FIG. 1 shows a structural diagram of a strategic arrangement of Helz2-Cas9-KO mice.

FIG. 1 shows a structural diagram of a strategic arrangement of Helz2-Cas9-KO mice. sgRNA sequences for Helz2 knockout process can be selected based on the coding exons shown in FIG. 1.

In some embodiments, the method for establishing an Helz2 knockout mouse model includes the following steps.

S1: determining recognition sequences of sgRNA for Helz2 in targeting mice, and constructing sgRNA; after determining a specific knockout region by analyzing Helz2, determining a pair of corresponding sgRNA sequences according to the target Helz2 gene, and synthesizing the sgRNA sequences; and transcribing the synthesized sgRNA sequences into mRNA in vitro. The sgRNA sequences include one or more of the following sequences.

```
SEQ ID No. 1:
5'-GCCCCAGAGTTACCAGATGGAGG-3';

SEQ ID No. 2:
5'-CCTACACCCGACAGAGGTGTAGG-3';

SEQ ID No. 3:
5'-AGCAGTGACAGTCTTATGGGTGG-3';

SEQ ID No. 4:
5'-GGCATACAGAGGATTGCCACAGG-3'.
```

S2: injecting the mRNA obtained in S1 and Cas9 plasmids into fertilized mouse eggs by microinjection, and obtaining F0-generation mice through cultivation;

S3: screening out positive F0-generation mice by PCR and sequencing identification; and S4: making the F0-generation mice mate and breed after sexual maturation to obtain positive F1-generation mice.

Figure 2:
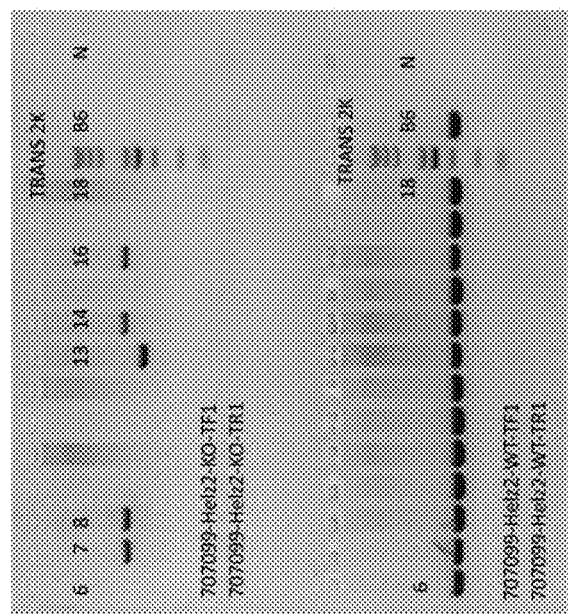
FIG. 2 shows electrophoretic results of an example experiment conducted consistent with the present disclosure.

FIG. 2 shows electrophoretic results of an example experiment conducted based on the method described above. As shown in FIG. 2, B6 is B6 genomic DNA as negative control; N is a no template control as a blank control; TRANS 2K PLUS II DNA marker: 8,000 bp, 5,000 bp, 3,000 bp, 2,000 bp, 1,000 bp, 750 bp, 500 bp, 250 bp and 100 bp. Two pairs of primers (707099-Helz2-KO-TF1 and 707099-Helz2-KO-TR1; 707099-Helz2-WT-TF1 and 707099-Helz2-WT-TR1 as shown in FIG. 2) were used in this experiment. In this experiment, sgRNA sequences of Seq ID. No. 1-4 are all used.

The present disclosure further provides an application of an Helz2 systemic knockout homozygous mouse model in preparation or screening of anti-tumor drugs and/or drugs for preventing tumors. The application includes screening of drug targets, screening of drugs, pharmacodynamic evaluation of drugs and safety evaluation of drugs.

The present disclosure further provides an sgRNA sequence for establishing an Helz2 knockout animal model, including one or more of the following SEQ ID No.1 to SEQ ID No.4 gene sequences:

```
SEQ ID No. 1:
5'-GCCCCAGAGTTACCAGATGGAGG-3';

SEQ ID No. 2:
5'-CCTACACCCGACAGAGGTGTAGG-3';

SEQ ID No. 3:
5'-AGCAGTGACAGTCTTATGGGTGG-3';

SEQ ID No. 4:
5'-GGCATACAGAGGATTGCCACAGG-3'.
```

The present disclosure further provides a vector containing a target sequence that targets and interferes with Helz2, and the target sequence is one or more of the following gene sequences:

```
SEQ ID No. 5:
5'-GCTATCAAGTCTGTCACTACT-3';

SEQ ID No. 6:
5'-GCACGATGCTGTATGGCTTTG-3';

SEQ ID No. 7:
5'-GGGCCTCATTGACACTCAAAG-3'.
```

The vector is one of lentiviral vector complex, adenovirus, adeno-associated virus, N-acetylgalactosamine (GalNAc), liposomes (LNPs), polymers and oncolytic viruses, or other biologically acceptable gene vectors.

The present disclosure further provides an application of the vector containing the sequence targeting Helz2 in preparation of biological agents for inhibiting expression of Helz2.

The present disclosure further provides a drug for treating and/or preventing tumors, where the drug contains a Helz2-targeting sequence or its expressed product.

In vivo tumor-bearing experiments in Helz2-Cas9-KO mice and shRNA interference-mediated Helz2-targeting therapy were conducted with tumor-bearing wild-type mice.

Example 1: Establishment of Mouse Models with Cells of a Mesothelioma Cell Line AE17

Firstly, 8 to 10-week-old mice were divided into two groups: a group of wild-type mice and a group of Helz2 knockout mice. Cells of a mesothelioma cell line AE17 in logarithmic growth phase were trypsinized and then washed with PBS one time, and the concentration of live cells was adjusted to $1 \times 10^5$ cells/100 µL. Afterwards, 100 µL of AE17 cell suspension was inoculated into abdominal cavities of the wild-type mice and the Helz2 knockout mice. The conditions of the mice were observed every day.

Figure 3:
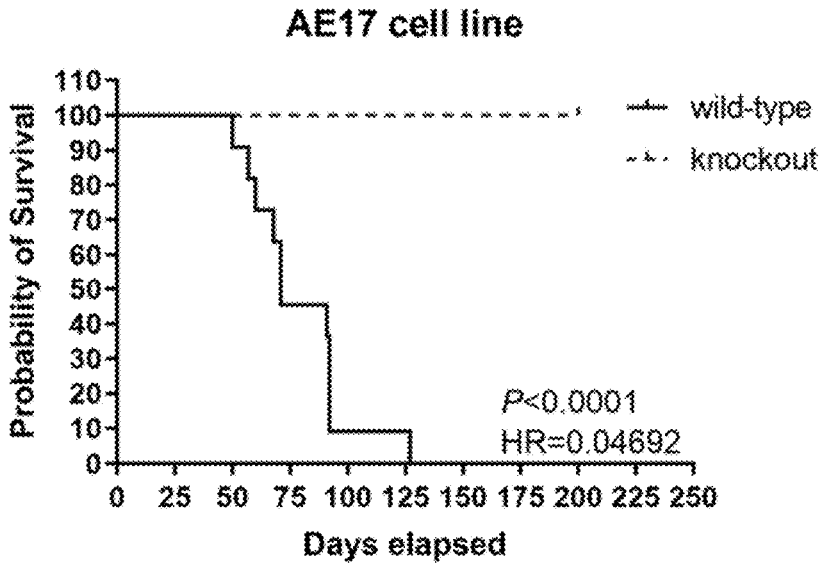
FIG. 3 shows a survival curve of tumor-bearing Helz2-Cas9-KO mice with mesothelioma AE17 in example 1.

The results showed that the wild-type mice began to die from Day 50 after tumor bearing, and all the wild-type mice were dead at Day 127; no obvious ascites, abnormality and death occurred in the Helz2 knockout mice throughout the entire observation period after tumor bearing, and the observation lasted to Day 200. These results indicate that the lifetime of the Helz2 knockout mice after tumor bearing can be obviously prolonged (P<0.001) as compared with that of the wild-type mice, suggesting that the Helz2 knockout mice have significant resistance to mesothelioma AE17, as shown in FIG. 3. The term HR, as used in FIGS. 3-11, is abbreviated from hazard ratio, which reflects a ratio of the hazard of death for the group of Helz2 knockout mice to the hazard of death for the group of wild-type mice.

Example 2: Establishment of Mouse Models with Cells of a Mesothelioma Cell Line 40 L Firstly, 8 to 10-week-old mice were divided into two groups: a group of wild-type mice and a group of Helz2 knockout mice. Cells of a mesothelioma cell line 40 L in logarithmic growth phase were trypsinized and then washed with PBS one time, and the concentration of live cells was adjusted to $2 \times 10^5$ cells/100 µL. Afterwards, 100 µL of 40 L cell suspension was inoculated into abdominal cavities of the wild-type mice and the Helz2 knockout mice. The conditions of the mice were observed every day.

Figure 4:
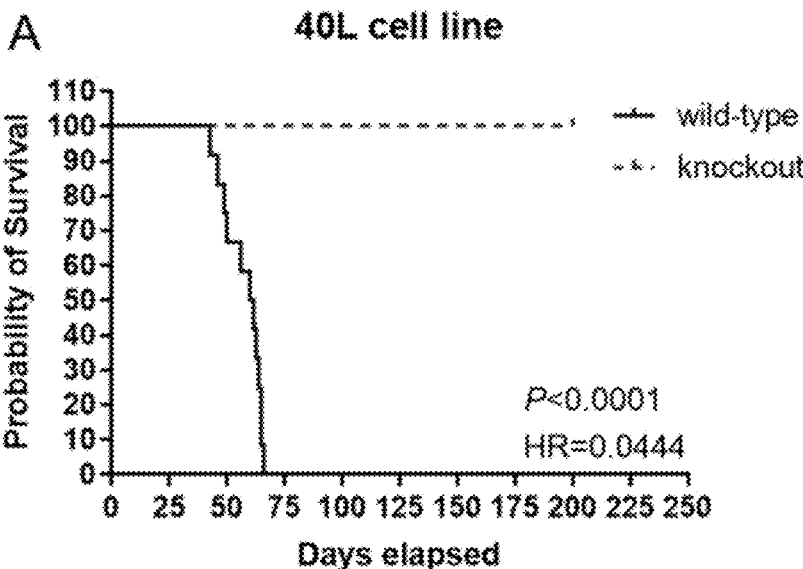
FIG. 4 shows a survival curve of tumor-bearing Helz2-Cas9-KO mice with mesothelioma 40 L in example 2.

The results showed that the wild-type mice began to die from Day 43 after tumor bearing, and all the wild-type mice were dead at Day 66; no obvious ascites, abnormality and death occurred in the Helz2 knockout mice throughout the entire observation period after tumor bearing, and the observation lasted to Day 200. These results indicate that the lifetime of the Helz2 knockout mice after tumor bearing can be obviously prolonged (P<0.001) as compared with that of the wild-type mice, suggesting that the Helz2 knockout mice have significant resistance to mesothelioma 40 L, as shown in FIG. 4.

Example 3: Establishment of Mouse Models with Cells of an Ovarian Cancer Cell Line ID8

Firstly, 8 to 10-week-old mice were divided into two groups: a group of wild-type mice and A group of Helz2 knockout mice. Cells of an ovarian cancer cell line ID8 in logarithmic growth phase were trypsinized and then washed with PBS one time, and the concentration of live cells was adjusted to $1 \times 10^6$ cells/100 µL. Afterwards, 100 µL of ID8 cell suspension was inoculated into abdominal cavities of the wild-type mice and the Helz2 knockout mice. The conditions of the mice were observed every day.

Figure 5:
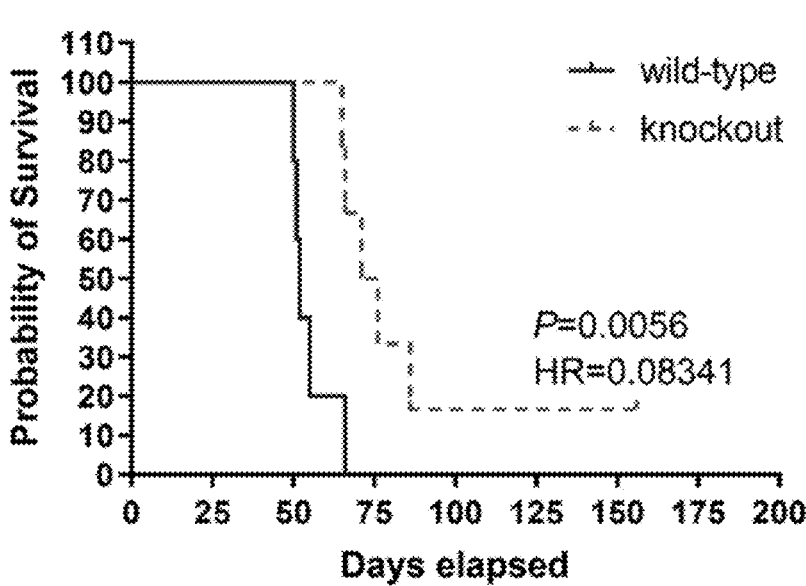
FIG. 5 shows a survival curve of tumor-bearing Helz2-Cas9-KO mice with ovarian cancer ID8 in example 3.

The results showed that the wild-type mice began to die from Day 50 after tumor bearing, and all the wild-type mice were dead at Day 66; the Helz2 knockout mice began to die from Day after tumor bearing, the last dead Helz2 knockout mouse died at Day 86, the remaining one Helz2 knockout mouse had no obvious ascites, abnormality and death throughout the entire observation period after tumor bearing, and the observation lasted to Day 156. These results indicate that the lifetime of the Helz2 knockout mice after tumor bearing can be obviously prolonged (P=0.0056) as compared with that of the wild-type mice, suggesting that the Helz2 knockout mice have significant resistance to ovarian cancer ID8, as shown in FIG. 5.

Example 4: Establishment of Mouse Models with Cells of a Lung Cancer Cell Line Lewis Firstly, 8 to 10-week-old mice were divided into two groups: a group of wild-type mice and A group of Helz2 knockout mice. Cells of a lung cancer cell line Lewis in logarithmic growth phase were trypsinized and then washed with PBS one time, and the concentration of live cells was adjusted to $2 \times 10^6$ cells/100 µL. Afterwards, 100 µL of Lewis cell suspension was subcutaneously inoculated at the right shoulders of the wild-type mice and the Helz2 knockout mice. The conditions of the mice were observed every day.

Figure 6:
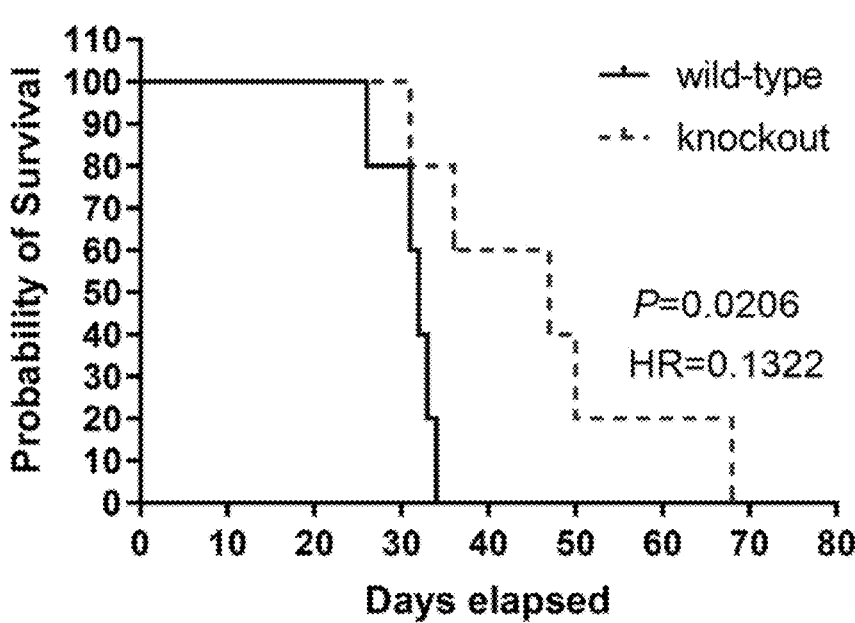
FIG. 6 shows a survival curve of tumor-bearing Helz2-Cas9-KO mice with lung cancer Lewis in example 4.

The results showed that the wild-type mice began to die from Day 26 after tumor bearing, and all the wild-type mice were dead at Day 34; the Helz2 knockout mice began to die from Day 31 after tumor bearing, and all the Helz2 knockout mice were dead at Day 68. These results indicate that the lifetime of the Helz2 knockout mice after tumor bearing can be obviously prolonged (P=0.0206) as compared with the wild-type mice, and the tumor growth is effectively inhibited in the Helz2 knockout mice, suggesting that the Helz2 knockout mice have significant resistance to lung cancer Lewis, as shown in FIG. 6.

Example 5: Establishment of Mouse Models with Cells of a Breast Cancer Cell Line E0771

Firstly, 8 to 10-week-old mice were divided into two groups: a group of wild-type mice and A group of Helz2 knockout mice. Cells of a breast cancer cell line E0771 in logarithmic growth phase were trypsinized and then washed with PBS one time, and the concentration of live cells was adjusted to $8 \times 10^4$ cells/100 µL. Afterwards, 100 µL of E0771 cell suspension was inoculated into abdominal cavities of the wild-type mice and the Helz2 knockout mice. The conditions of the mice were observed every day.

Figure 7:
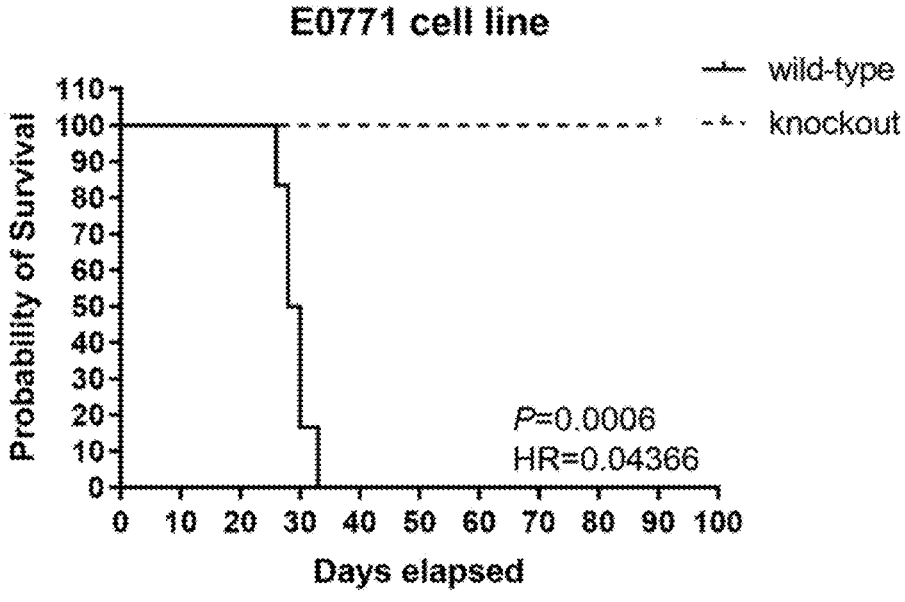
FIG. 7 shows a survival curve of tumor-bearing Helz2-Cas9-KO mice with breast cancer E0771 in example 5.

The results showed that the wild-type mice began to die from Day 26 after tumor bearing, and all the wild-type mice were dead at Day 33; no obvious ascites, abnormality and death occurred in the Helz2 knockout mice throughout the entire observation period after tumor bearing, and the observation lasted to Day 90. These results indicate that the lifetime of the Helz2 knockout mice after tumor bearing can be obviously prolonged (P=0.0006) as compared with that of the wild-type mice, suggesting that the Helz2 knockout mice have significant resistance to breast cancer E0771, as shown in FIG. 7.

Example 6: Establishment of Mouse Models with Cells of a Pancreatic Cancer Cell Line Panc02

Firstly, 8 to 10-week-old mice were divided into two groups: a group of wild-type mice and A group of Helz2 knockout mice. Cells of a pancreatic cancer cell line Panc02 in logarithmic growth phase were trypsinized and then washed with PBS one time, and the concentration of live cells was adjusted to $8 \times 10^4$ cells/100 μL. Afterwards, 100 μL of Panc02 cell suspension was inoculated into abdominal cavities of the wild-type mice and the Helz2 knockout mice. The conditions of the mice were observed every day.

Figure 8:
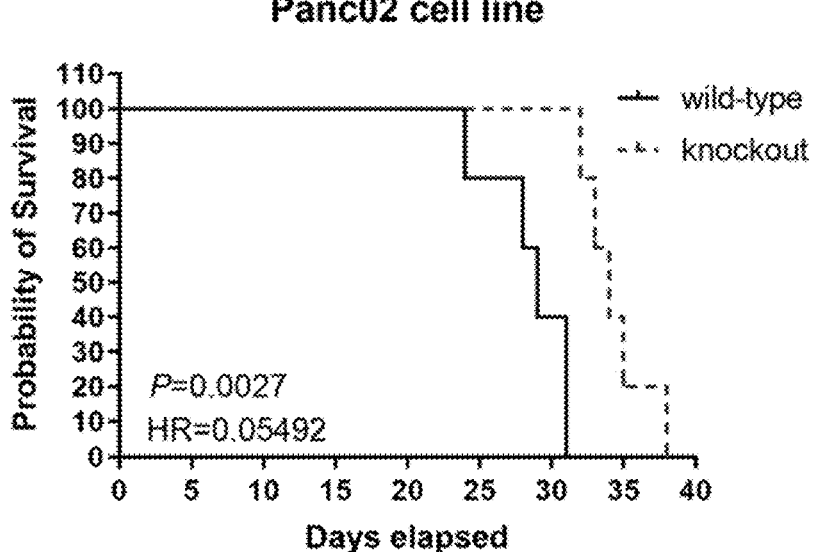
FIG. 8 shows a survival curve of the tumor-bearing Helz2-Cas9-KO mice with pancreatic cancer cell line Panc02 in example 6.

The results showed that the wild-type mice began to die from Day 24 after tumor bearing, and all the wild-type mice were dead at Day 31; the Helz2 knockout mice began to die from Day 32 after tumor bearing, and all the Helz2 knockout mice were dead at Day 38. These results indicate that the lifetime of the Helz2 knockout mice after tumor bearing can be obviously prolonged (P=0.0027) as compared with that of the wild-type mice, and the tumor growth is effectively inhibited in the Helz2 knockout mice, suggesting that the Helz2 knockout mice have significant resistance to pancreatic cancer Panc02, as shown in FIG. 8.

Example 7: Establishment of Cells of a Mesothelioma Cell Line AE17 with Stable Helz2 Knockdown by Lentiviral Infection (Sh-Helz2-AE17)

AE17 cells in logarithmic growth phase were inoculated into a 96-well plate at 2,000 cells per well. The AE17 cells were infected by sh-Helz2 when the cell density was 40%-60%, and three duplicate wells were set for each group; AE17 cells infected by sh-NC were used as a control group (sh-NC-AE17). A lentivirus stock solution with a titer of $10^8$ was diluted to produce virus solutions of three gradients: the stock solution, 10× diluted solution and 100× diluted solution. 10 μL of virus solutions of such three different concentrations were added to the three duplicate wells in each group, 1:1,000 polybrene (with a final concentration of 5 μg/ml) was add to each well, and the mixture was mixed well in a cross manner. Then the cells were put back in a cell incubator for incubation. A fresh medium was changed after 24 h. After 72-96 h of infection, the expression of fluorescence was observed, and the optimal dilution factor for infecting the cells was determined through a pre-experiment. The experiment found that the optimal concentration for infecting the AE17 cells was the stock solution, so that the stock solution concentration was used for formal infection process.

A pre-experiment for determining a minimum cell-killing amount of puromycin was performed for 72 h before the formal infection process. The AE17 cells were cultured in a 24-well plate to reach the logarithmic growth phase in advance, puromycin of different concentrations (1 μg/ml, 2 μg/ml, 3 μg/ml, 4 μg/ml, 5 μg/ml, 6 μg/ml, 7 μg/ml, 8 μg/ml, 9 μg/ml and 10 μg/ml) was added, and the minimum cell-killing concentration was selected after 72 h. The minimum cell-killing concentration selected in the experiment was 3 μg/m. The infected AE17 cells were continuously cultured for one week, the AE17 cells were digested and transferred from a 96-well plate to 6-well plates for puromycin screening, and the screened AE17 cells were cultured for one month to obtain the AE17 cells with stable Helz2 knockdown (sh-Helz2-AE17 cells).

Example 8: Establishment of Tumor-Bearing Wild-Type Mouse Models with Lentivirus-Infected AE17 Cells (Sh-NC-AE17 Cells and Sh-Helz2-AE17 Cells)

Firstly, 8 to 10-week-old wild-type mice were divided into two groups: sh-NC-AE17 group and sh-Helz2-AE17 group.

The sh-NC-AE17 cells and the sh-Helz2-AE17 cells in logarithmic growth phase were trypsinized and then washed with PBS one time, and the concentration of live cells was adjusted to $3 \times 10^5$ cells/100 μL. Afterwards, 100 μL of sh-NC-AE17 cell suspension and 100 μL of sh-Helz2-AE17 cell suspension were inoculated into abdominal cavities of the wild-type mice, respectively. The conditions of the mice were observed every day.

Figure 9:
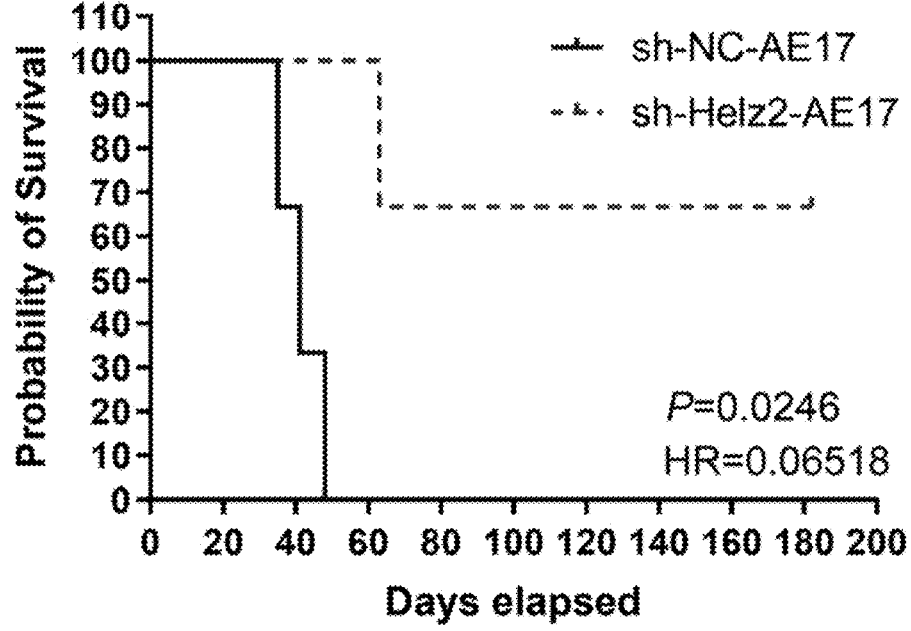
FIG. 9 shows a survival curve of the tumor-bearing wild-type mice with sh-NC-AE17 and sh-Helz2-AE17 cells in example 8.

The results showed that the mice in the sh-NC-AE17 group began to die from Day 35 after tumor bearing, and all the mice in the sh-NC-AE17 group were dead at Day 48; one mouse in the sh-Helz2-AE17 group died at Day 63 after tumor bearing, the remaining mice had no obvious ascites and abnormality until the last day of observation, and the observation lasted to Day 182. These results indicate that as compared with the sh-NC-AE17 group, the lifetime of the tumor-bearing mice in the sh-Helz2-AE17 group can be significantly prolonged (P=0.0246), suggesting that the tumor-forming ability is significantly weakened in the AE17 cells infected by the lentivirus sh-Helz2, as shown in FIG. 9.

Example 9: shRNA Interference-Mediated Helz2-Targeting Treatment of AE17 Tumor-Bearing Wild-Type Mice Firstly, 8 to 10-week-old wild-type mice were divided into four groups: sh-NC control group, sh-Helz2-1 treatment group, sh-Helz2-2 treatment group and sh-Helz2-3 treatment group. Here, sh-Helz2-1 treatment group corresponds to the group that received treatment of a vector containing target sequence with SEQ ID No.5, sh-Helz2-2 treatment group corresponds to the group that received treatment of a vector containing target sequence with SEQ ID No.6, sh-Helz2-3 treatment group corresponds to the group that received treatment of a vector containing target sequence with SEQ ID No.7. Cells of a mesothelioma cell line AE17 in logarithmic growth phase were trypsinized and then washed with PBS one time, and the concentration of live cells was adjusted to $1 \times 10^5$ cells/100 μL. Afterwards, 100 μL of AE17 cell suspension was inoculated into abdominal cavities of the wild-type mice, respectively.

Figures 10, 11:
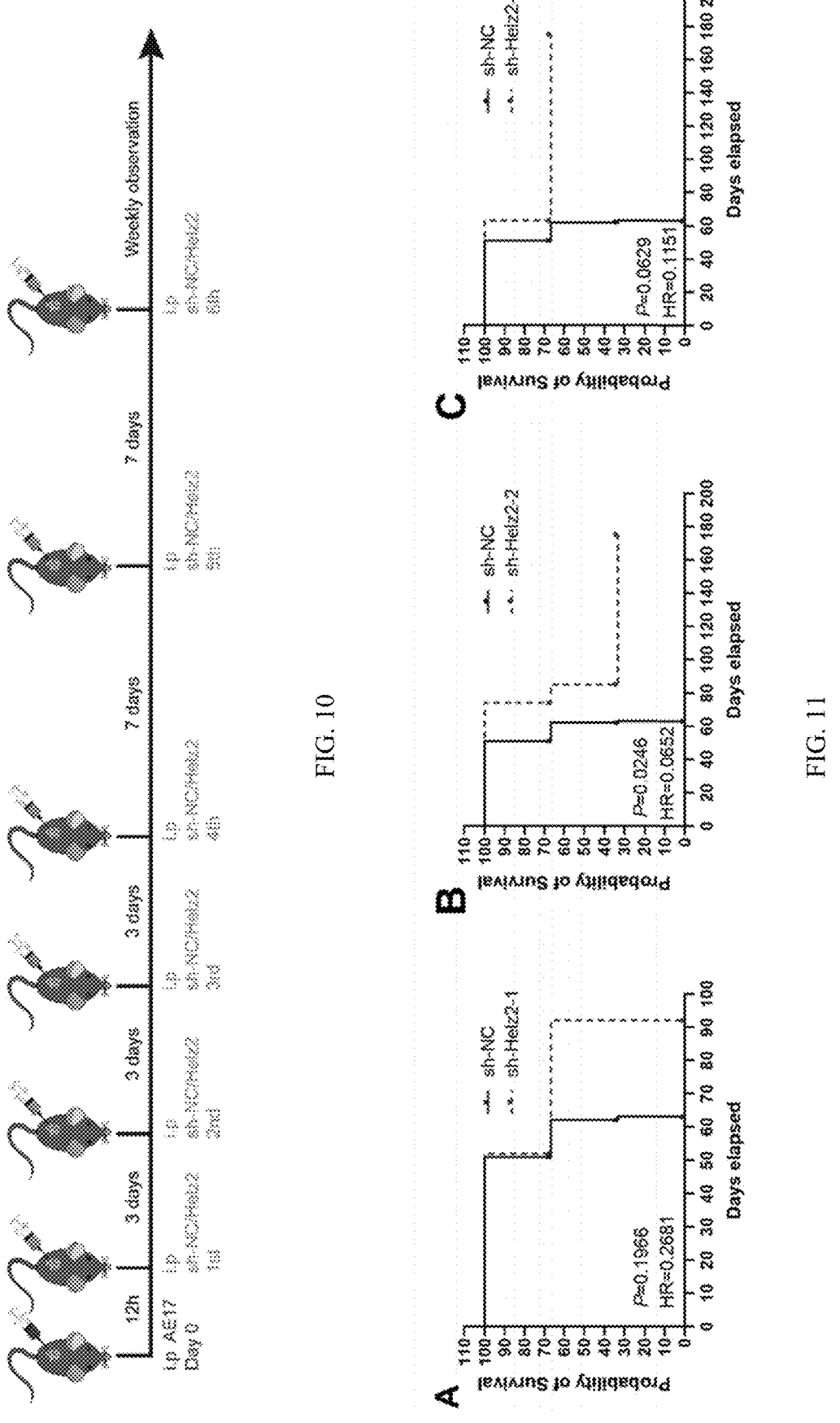
FIG. 10 is a mode pattern of sh-Helz2 in treating AE17 tumor-bearing wild-type mice in example 9.
FIG. 11 shows a survival curve of AE17 tumor-bearing wild-type mice treated by sh-Helz2 in example 9.

10 μL of sh-NC lentiviral stock solution and 10 μL of sh-Helz2 lentiviral stock solution with a titer of $10^8$ were added to 90 μL of sterile PBS for dilution, respectively, and 100 μL of sh-NC lentiviral working solution and 100 μL of sh-Helz2 lentiviral working solution were obtained correspondingly. At 12 h after the tumor cells were inoculated, the sh-NC lentiviral working solution and sh-Helz2 lentiviral working solution were injected into abdominal cavities of the tumor-bearing wild-type mice, respectively, and the injection volume was 100 μL of lentiviral working solutions as diluted above. This was the $1^{st}$ treatment using sh-Helz2 lentivirus. The treatment was repeated in accordance with the $1^{st}$ treatment at an interval of $3^{rd}$ from the $1^{st}$ treatment as the $2^{nd}$ treatment using the sh-Helz2 lentivirus. The $3^{rd}$ treatment using the sh-Helz2 lentivirus was repeated in accordance with the $1^{st}$ treatment at an interval of $3^{rd}$ from the $2^{nd}$ treatment The $4^{th}$ treatment using the sh-Helz2 lentivirus was repeated in accordance with the $1^{st}$ treatment at an interval of 3 d from the $3^{rd}$ treatment. The $5^{th}$ treatment using the sh-Helz2 lentivirus was repeated in accordance with the $1^{st}$ treatment at an interval of 7 d from the $4^{th}$ treatment. The $6^{th}$ treatment using the sh-Helz2 lentivirus was repeated in accordance with the $1^{st}$ treatment at an interval of 7 d from the $5^{th}$ treatment. The time intervals of the treatment were as shown in FIG. 10, and the treatments were performed for a total of six times.

The results showed that the tumor-bearing mice in the sh-NC control group began to die from Day 51, and all the mice in the sh-NC control group were dead at Day 63; the tumor-bearing mice in the sh-Helz2-1 treatment group began to die from Day 52, and all the mice in the sh-Helz2-1 treatment group were dead at Day 92 (P=0.1966); the tumor-bearing mice in the sh-Helz2-2 treatment group began to die from Day 74, the remaining one mouse had no obvious ascites and abnormality until the last day of observation, and the observation lasted to Day 175 (P=0.0246); the tumor-bearing mice in the sh-Helz2-3 treatment group began to die from Day 63, the remaining two mice had no obvious ascites and abnormality until the last day of observation, and the observation lasted to Day 175 (P=0.0629). These results indicate that the lifetime of the tumor-bearing mice in the sh-Helz2 treatment groups can be significantly prolonged as compared with the sh-NC control group, suggesting that the lentivirus-carrying shRNA (sh-Helz2) developed targeting Helz2 can effectively treat the tumor-bearing mice, prolong the lifetime and improve the survival quality, as shown in FIG. 11.

Figure 12:
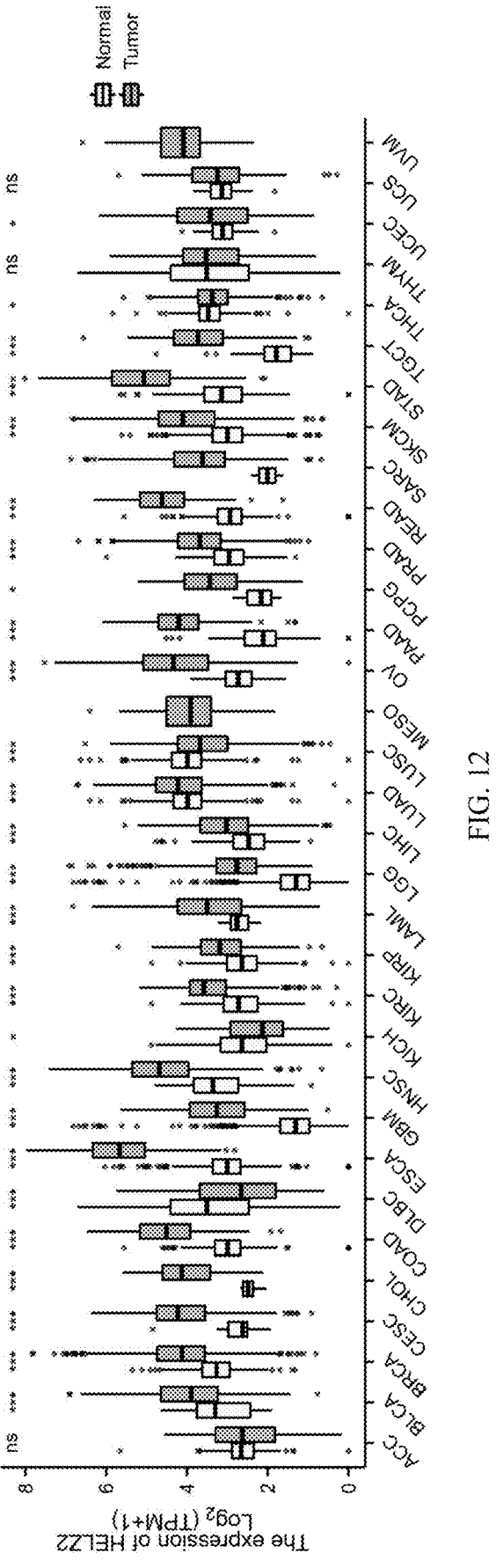
FIG. 12 shows expression of Helz2 in pan-cancer in example 10.

Example 10: to explore the expression of Helz2 in other types of tumors, a total of 15,776 samples were analyzed using The Cancer Genome Atlas (TCGA) database and Genotype-Tissue Expression (GTEx) database. The results showed that Helz2 was highly expressed in 25 cancers (*P<0.05; P<0.01; *P<0.001), including bladder urothelial carcinoma (BLCA), breast invasive carcinoma (BRCA), cervical squamous cell carcinoma and endocervical adenocarcinoma (CESC), cholangiocarcinoma (CHOL), colon adenocarcinoma (COAD), esophageal carcinoma (ESCA), glioblastoma multiforme (GBM), head and neck squamous cell carcinoma (HNSC), kidney renal clear cell carcinoma (KIRC), kidney renal papillary cell carcinoma (KIRP), acute myeloid leukemia (LAML), brain low-grade glioma (LGG), liver hepatocellular carcinoma (LIHC), lung adenocarcinoma (LUAD), ovarian serous cystadenocarcinoma (OV), pancreatic cancer (PAAD), pheochromocytoma and paraganglioma (PCPG), prostate adenocarcinoma (PRAD), rectum adenocarcinoma (READ), sarcoma (SARC), skin cutaneous melanoma (SKCM), stomach adenocarcinoma (STAD), testicular germ cell tumors (TGCT), thyroid carcinoma (THCA) and uterine corpus endometrial carcinoma (UCEC), as shown in FIG. 12, suggesting that in these tumors, the interferences to the Helz2 target also have the same effect on treating tumors as those in examples 1-9.

The present disclosure provides a key target Helz2 for treating and/or preventing tumors. With the help of the CRISPR/Cas9 gene technology and the shRNA interference technology, an Helz2-Cas9-KO mouse model is established and a new Helz2-targeting therapy in treating tumors is provided. Through in vivo tumor-bearing experiments in Helz2-Cas9-KO mice and shRNA interference-mediated Helz2-targeting therapy in tumor-bearing wild-type mice, it was confirmed that knocking out Helz2 could significantly inhibit the growth of tumor cells and prolong the lifetime of the mice.

The present disclosure provides a reliable animal model for illustrating the action mechanism of Helz2 in the occurrence and development of tumors, provides a clinical target for Helz2 in the screening and preparation of drugs for treating and/or preventing tumors, and also provides a new therapy of Helz2 in treating tumors, thereby having broad application prospects.

Those skilled in the art should understand that the modifications and variations of the various embodiments disclosed above can be made without departing from the essence of the invention. Therefore, the protection scope of the present disclosure should be defined by the appended claims.

Although different exemplary embodiments of the present disclosure have been described, it is obvious to those skilled in the art that various changes and modifications can be made, which can achieve some of the advantages of the present disclosure without departing from the spirit and scope of the present disclosure. For those who are quite skilled in the art, other components performing the same function can be replaced as appropriate. It should be mentioned that the features explained here with reference to particular figures can be combined with features of other figures, even in those cases where this is not explicitly mentioned. In addition, the method of the present disclosure can be implemented either in all software implementations using appropriate processor instructions or in a hybrid implementation using a combination of hardware logic and software logic to achieve the same result. Such modifications to the solution according to the invention are intended to be covered by the appended claims.

What is claimed is:

1. A vector containing a target sequence that targets and interferes with Helicase with zinc finger 2 (Helz2), the target sequence comprising one or more of the following sequences:

```
SEQ ID No. 5:
5'-GCTATCAAGTCTGTCACTACT-3';

SEQ ID No. 6:
5'-GCACGATGCTGTATGGCTTTG-3';

SEQ ID No. 7:
5'-GGGCCTCATTGACACTCAAAG-3'.
```

2. The vector according to claim 1, wherein the vector is a biologically acceptable vector and is one of lentiviral vector complex, adenovirus, adeno-associated virus, N-acetylgalactosamine (GalNAc), liposomes (LNPs), polymers, and oncolytic viruses.

3. A method for establishing an Helz2 knockout mouse model, comprising:

performing Helz2 knockout on fertilized mouse eggs by using CRISPR/Cas9 technique with an sgRNA sequence; and obtaining a systemic Helz2 knockout homozygous mouse model through microinjection and breeding of the fertilized mouse eggs, wherein the sgRNA sequence comprises one or more of the following sequences:

```
SEQ ID No. 1:
5'-GCCCCAGAGTTACCAGATGGAGG-3';

SEQ ID No. 2:
5'-CCTACACCCGACAGAGGTGTAGG-3';

SEQ ID No. 3:
5'-AGCAGTGACAGTCTTATGGGTGG-3';

SEQ ID No. 4:
5'-GGCATACAGAGGATTGCCACAGG-3'.
```

4. An sgRNA sequence for establishing an Helz2 knockout animal model, comprising one or more of the following sequences:

```
SEQ ID No. 1:
5'-GCCCCAGAGTTACCAGATGGAGG-3';

SEQ ID No. 2:
5'-CCTACACCCGACAGAGGTGTAGG-3';

SEQ ID No. 3:
5'-AGCAGTGACAGTCTTATGGGTGG-3';

SEQ ID No. 4:
5'-GGCATACAGAGGATTGCCACAGG-3'.
```

* * * * *

```
                          SEQUENCE LISTING

Sequence total quantity: 7
SEQ ID NO: 1            moltype = RNA  length = 23
FEATURE                Location/Qualifiers
source                 1..23
                       mol_type = other RNA
                       organism = synthetic construct
SEQUENCE: 1
gccccagagt taccagatgg agg                                       23

SEQ ID NO: 2            moltype = RNA  length = 23
FEATURE                Location/Qualifiers
source                 1..23
                       mol_type = other RNA
                       organism = synthetic construct
SEQUENCE: 2
cctacacccg acagaggtgt agg                                       23

SEQ ID NO: 3            moltype = RNA  length = 23
FEATURE                Location/Qualifiers
source                 1..23
                       mol_type = other RNA
                       organism = synthetic construct
```

-continued

```
SEQUENCE: 3
agcagtgaca gtcttatggg tgg                                                        23

SEQ ID NO: 4              moltype = RNA  length = 23
FEATURE                   Location/Qualifiers
source                    1..23
                          mol_type = other RNA
                          organism = synthetic construct
SEQUENCE: 4
ggcatacaga ggattgccac agg                                                        23

SEQ ID NO: 5              moltype = RNA  length = 21
FEATURE                   Location/Qualifiers
source                    1..21
                          mol_type = other RNA
                          organism = synthetic construct
SEQUENCE: 5
gctatcaagt ctgtcactac t                                                          21

SEQ ID NO: 6              moltype = RNA  length = 21
FEATURE                   Location/Qualifiers
source                    1..21
                          mol_type = other RNA
                          organism = synthetic construct
SEQUENCE: 6
gcacgatgct gtatggcttt g                                                          21

SEQ ID NO: 7              moltype = RNA  length = 21
FEATURE                   Location/Qualifiers
source                    1..21
                          mol_type = other RNA
                          organism = synthetic construct
SEQUENCE: 7
gggcctcatt gacactcaaa g                                                          21
```